(12) United States Patent
Gamble

(10) Patent No.: US 8,311,313 B1
(45) Date of Patent: Nov. 13, 2012

(54) IMAGING INSPECTION APPARATUS INCORPORATING A DEVICE FOR SOLVING CUBIC POLYNOMIALS

(75) Inventor: Thomas D. Gamble, Annandale, VA (US)

(73) Assignee: SureScan Corporation, Endicott, NY (US)

( * ) Notice: Subject to any disclaimer, the term of this patent is extended or adjusted under 35 U.S.C. 154(b) by 480 days.

(21) Appl. No.: 12/701,941

(22) Filed: Feb. 8, 2010

(51) Int. Cl.
*G06K 9/00* (2006.01)

(52) U.S. Cl. .......................................... 382/141; 382/152

(58) Field of Classification Search .................. 382/131, 382/132, 141–152
See application file for complete search history.

(56) References Cited

U.S. PATENT DOCUMENTS

| | | | |
|---|---|---|---|
| 5,524,133 A | 6/1996 | Neale et al. | |
| 5,991,358 A | 11/1999 | Dolazza et al. | |
| 6,018,562 A | 1/2000 | Willson | |
| 6,236,709 B1 | 5/2001 | Perry et al. | |
| 7,177,391 B2 | 2/2007 | Chapin et al. | |

*Primary Examiner* — Tri T Ton
(74) *Attorney, Agent, or Firm* — Mark Levy; Hinman, Howard & Kattell, LLP

(57) ABSTRACT

An imaging inspection machine for inspecting objects located within articles, with the imaging inspection machine having an inspection location for articles having a quantity of objects located along a path of travel through an inspection location located within the imaging inspection machine. Imaging inspection devices are positioned on the frame and adapted for directing beams through articles as articles move through the inspection location within the imaging inspection machine. As a result of inspecting the articles, output signals are applied to a processing and analysis assembly which performs only simple table lookups into an appropriately formed table and one multiplication for each pixel to correct nonlinearities matched by a cubic polynomial.

12 Claims, 3 Drawing Sheets

IMAGING INSPECTION APPARATUS INCORPORATING A DEVICE FOR SOLVING CUBIC POLYNOMIALS

FIELD OF THE INVENTION

The present invention relates to photon radiation detectors and, more particularly, to efficient correction of detector nonlinearities matched by cubic polynomials.

BACKGROUND OF THE INVENTION

Cubic or third degree equations were known to the ancient Indians and ancient Greeks since the 5th century BC, and even earlier to the ancient Egyptians, who dealt with the problem of doubling the cube, and attempted to solve it using compass and straightedge constructions.

In the early 16th century, the Italian mathematician Scipione del Ferro (1465-1526) found a method for solving a class of cubic equations, namely those of the form $x^3+mx=n$. In fact, all cubic equations can be reduced to this form if m and n can be negative. Solution involves complex arithmetic, various conditional tests, extraction of roots and trigonometric functions. Modern general processing units can solve such equations tens of thousands of times per second. However, high speed imaging systems may generate tens of millions of pixel values per second. If their nonlinearities are sufficiently complex that a good fit requires a cubic polynomial, correction of their nonlinearities in real time by the general solution of those polynomials would require expensive, custom computational resources.

A numerical table to approximately invert a homogeneous cubic polynomial would be expected to be three dimensional to accommodate arbitrary values of the three coefficients. Such a table to correct to 1% accuracy would require many megabytes of memory, making storage and access to the table slower and more expensive. The present invention defines a method of reducing the form of an arbitrary cubic polynomial to a timing parameter and a dimensionless shape parameter which permits tabulation of all cubic polynomials in a two dimensional table and rapid correction to 1% accuracy with a table occupying tens of kilobytes. The table lookup then required to correct the nonlinearities could be implemented on hardware less capable than a general purpose CPU.

The use of imaging inspection apparatus is known, including those which utilize X-ray imaging. Such apparatus are used to inspect articles such as personal luggage of airplane travelers for such undesirable items as explosives, weapons, and drugs.

One particularly successful example of such a method is that which utilizes what is referred to in the art as "X-ray Computer Tomography" apparatus (hereinafter also referred to as XCT). XCT apparatus are in wide use in the medical field for providing medical imaging such as patient body X-rays. XCT, referred to in the medical profession simply as "CT scanning," produces a cross sectional image from a grouping of attenuation measurements taken at different angles about an object such as a patient's chest or head, while the patient is maintained in a stationary position.

Modifications have been made to such apparatus to make them adaptable to taking images for non-medical purposes. In order to make such apparatus capable of even higher speed scanning than provided by conventional stationary apparatus, such as that useful for scanning the luggage of large numbers of travelers in a relatively shorter time period, further modifications have been made.

One such apparatus is described in U.S. Pat. No. 6,236,709, for CONTINUOUS HIGH SPEED TOMOGRAPHIC IMAGING SYSTEM AND METHOD issued to Perry et al. on May 22, 2001, in which a continuous, XCT imaging system includes a conveyor which moves a closed package along the conveyor past three spaced sensing stations. At each sensing station a plurality of X-ray sources each emit a fan beam in the same scan plane which passes through the package to a plurality of detectors opposite the X-ray sources. One scan is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a Computer Tomographic algebraic reconstruction technique, where the density of a reconstructed object is determined by the attenuation which it causes in the scanning X-rays. The atomic number of the object is determined from the multiple energy scan output. In a classifier, the density and atomic number are compared to a table containing density and atomic number identification values for specific objects to be located.

Other examples of various scanning apparatus systems, including those with and without conveyors, are shown and described in the following U.S. patents.

U.S. Pat. No. 6,018,562, for APPARATUS AND METHOD FOR AUTOMATIC RECOGNITION OF CONCEALED OBJECTS USING MULTIPLE ENERGY COMPUTED TOMOGRAPHY issued to Willson on Jan. 25, 2000, describes an apparatus for automatic recognition and identification of concealed objects and features thereof, such as contraband in baggage or defects in articles of manufacture. The apparatus uses multiple energy X-ray scanning to identify targets with a spectral response corresponding to a known response of targets of interest. Detection sensitivity for both automatic detection and manual inspection are improved through the multiple-energy, multi-spectral technique. Multichannel processing is used to achieve high throughput capability. Target identification may be verified through further analysis of such attributes as shape, texture, and context of the scan data. The apparatus uses a statistical analysis to predict the confidence level of a particular target identification. A radiograph, CT image, or both may be reconstructed and displayed on a computer monitor for visual analysis by the apparatus operator. Finally, the apparatus may receive and store input from the operator for use in subsequent target identification.

U.S. Pat. No. 5,991,358, for DATA ACQUISITION SYSTEM FOR GENERATING ACCURATE PROJECTION DATA IN A CT SCANNER issued to Dolazza et al. on Nov. 23, 1999, describes a data acquisition system for use in a CT scanner which consists of an analog-to-digital converter for generating digital signals in response to analog signals representative of projection data taken at a relatively constant sampling rate. The apparatus also uses an interpolation filter for generating projection data for a plurality of predetermined projection angles as a function of the digital signals irrespective of the sampling rate. This patent references a known system which includes an array of individual detectors disposed as a single row in the shape of an arc of a circle having a center of curvature at a certain point, referred to as the "focal spot," where the radiation emanates from the X-ray source.

The X-ray source and the array of detectors in this known system are positioned so that the X-ray paths between the source and each of the detectors all lie in the same plane (hereinafter the "rotation plane" or "scanning plane") which is normal to the rotation axis of the disk. Since the X-ray paths originate from what is substantially a point source and extend at different angles to the detectors, the X-ray paths form a "fan beam." The X-rays incident on a single detector at a measuring interval during a scan are commonly referred to as a "ray," and each detector generates an analog output signal indicative of the intensity of its corresponding ray. Since each ray is partially attenuated by all the mass in its path, the analog output signal generated by each detector is representative of an integral of the density of all the mass disposed between that detector and the X-ray source (i.e., the density of the mass lying in the detector's corresponding ray path) for that measuring interval.

U.S. Pat. No. 5,524,133, for MATERIAL IDENTIFICATION USING X-RAYS issued to Neale et al. on Jun. 4, 1996, describes an X-ray analysis device for determining the mean atomic number of a material mass by locating a broad band X-ray source on one side of a testing station and on the other, a detector, comprising a target having X-ray detectors positioned adjacent thereto. One of the detectors is positioned and adapted to receive X-rays scattered by the detector target in a generally rearward direction and the other detector is positioned and adapted to detect forwardly propagating X-rays scattered off axis typically by more than 30 degrees, due to so-called "Compton scatter." Each of the X-ray detectors provides signals proportional to the number of X-ray photons incident thereon. The apparatus further includes means responsive to the two detector outputs which form a ratio of the number of photons detected by the two detectors and forms a numerical value thereof. A look-up table containing mean atomic numbers for given numerical ratios for different materials is used, as is a means for determining from the look-up table the atomic number corresponding to the numerical ratio obtained from the outputs of the two detectors. The atomic number is provided as an output signal.

U.S. Pat. No. 7,177,391, for IMAGING INSPECTION APPARATUS issued to Chapin et al on Feb. 13, 2007, describes an imaging inspection apparatus that utilizes a plurality of individual imaging inspection devices (e.g., X-ray Computer Tomography scanning devices) positioned on a frame for directing beams onto articles having objects therein to detect the objects based on established criteria. The apparatus utilizes a conveyor which is not physically coupled to the frame having the imaging inspection devices to pass the articles along a path of travel to an inspection location within the apparatus, whereupon the inspection devices direct beams onto the article and the beams are detected and output signals provided to a processing and analysis assembly which analyzes the signals and identifies certain objects which meet the criteria.

The above patents are incorporated herein by reference.

SUMMARY OF THE INVENTION

It is a primary object of the present invention to enhance the imaging inspection analysis art.

The present invention incorporates a unique method of correcting nonlinearities matched by cubic polynomials which, in one embodiment, uses imaging technology (e.g., XCT scanning) in combination with a moving conveyor which substantially corrects for variable detector responses under fluctuations of X-ray flux as luggage is moving along the conveyor and being inspected. The apparatus is thus able to more accurately determine the density and effective atomic number of the articles being scanned.

According to one embodiment of the invention, an imaging inspection apparatus is provided for inspecting objects located within moving articles, where the imaging inspection apparatus has a conveyor for moving the articles along a line of travel through an inspection location. The inspection location is within the imaging inspection apparatus, where the conveyor has a mainly flat orientation during the moving of the articles, a frame structure to support it, a grouping of imaging inspection devices positioned on the frame and adapted for directing beams onto the articles.

The articles continue to move on the conveyor and pass along the path of travel through the inspection location. In so doing, the articles are inspected. Output signals are generated as a result of this inspecting A processing and analysis assembly is adapted for receiving the output signals from the group of imaging inspection devices and for analyzing the output signals to identify the objects within the moving articles.

These and other problems are solved with a method and system according to the present invention in which some or all of relevant device parameters are calibrated by preprocessing gathered calibration data points to generate a polynomial equation of a curve which represents a particular parameter's characteristic response. As many calibration points are used as necessary to generate an accurate curve. During operation, this polynomial equation must be inverted to determine the actual, normalized linear inputs given the differing and possibly nonlinear responses of the image inspection devices. If all the devices can be accurately matched by possibly different, linear equations, this inversion can be performed rapidly. If quadratic or cubic equations are required, however, the inversions can still be performed analytically, but require much more computation and time. For the present high speed inspection application, millions of inversions are required per second and operation at high X-ray flux requires a cubic match to the nonlinearities. Analytic inversions are not practical.

Alternatively, a lookup table can contain the input values that would produce any possible output. This, in general, requires a dimension of the table for each of the polynomial coefficients (i.e., a four dimensional table for general cubic polynomials). Each dimension requires at least as many bins as the accuracy required in the inversion. Thus, if cubic polynomials and correction to 1% are required, tens of millions of words of computer storage are required. Due to hardware limitations of cache memory and data transfer rates, such a table is also not practical for high speed applications.

The current invention is a method of normalizing and structuring a lookup table for 1% inversion of all cubic equations in a two-dimensional rather than four-dimensional table, requiring only tens of thousands of data words, thus enabling rapid access and execution.

BRIEF DESCRIPTION OF THE DRAWINGS

A complete understanding of the present invention may be obtained by reference to the accompanying drawings, when considered in conjunction with the subsequent detailed description, in which.

For the sake of clarity and brevity, like elements and components of each embodiment will bear the same designations throughout the description.

DESCRIPTION OF THE PREFERRED EMBODIMENT

Generally speaking, the present invention relates to the field of study known as computerized X-ray tomography, or CAT scans, used in one instance as imaging inspection machines for determining if undesirable items have been incorporated in a person's luggage or freight. The system utilizes an imagining inspection apparatus having means for correcting detector non-linearity and reduces the difficulty of the current complexity for inverting a cubic polynomial to solve for the independent variable. A descriptive application of the present invention is described below with application to an X-ray tomography device, and beam current power levels in particular.

The processing and analysis assembly for the imaging apparatus of the invention can be similar to that used in U.S. Pat. No. 6,236,709, mentioned above. This assembly receives inputs from a sensor unit which includes the detector arrays. A preprocessing unit interfaces directly with the sensor units to provide buffering of the output data received from the sensor units. Timing is controlled by an input from a shaft encoder. Once the input has been received and stored by the preprocessing unit from each of the detector arrays for a single scan, an address generator in the preprocessing unit, which is connected to a plurality of reconstruction signal processing boards, generates a board address to determine which of the reconstruction signal processing boards receives a current frame of data. Each reconstruction board, as defined in U.S. Pat. No. 6,236,709, contains up to sixteen computer chips. These systems cooperate to provide calibration and normalization of the raw input data, and then multi-spectral XCT reconstruction which includes algebraic reconstruction.

The algebraic reconstruction data is then sent to a detection and segmentation section of the apparatus which detects the atomic number and density of a scanned object located within one of the articles. The linear X-ray attenuation coefficient $\mu$ is proportioned to the density. Thus the logarithm of the relative intensity of the X-ray beam is proportional to the integral of the density of the material within the beam. The density and atomic number information is compared in a classification unit with information (criteria) within a reference table containing density and atomic number information for specific objects to be identified. This identification data and the reconstructed image data are then sent preferably over a VME bus to a VME computer. The reconstructed XCT image data is displayed on the operator's console for review by the apparatus operator and others, if desired.

Calibration counts C(i) are collected at multiple flux levels f(i). For an ideal detector, the counts are proportional to the flux. In general, the observed counts can be fit by a polynomial: $C(i) = x_0 + x_1 f(i) + x_2 f(i)^2 + x_3 f(i)^3 + \ldots$. Linearization is the process of inverting this process to determine the flux when a count of C is observed.

Figure 1:
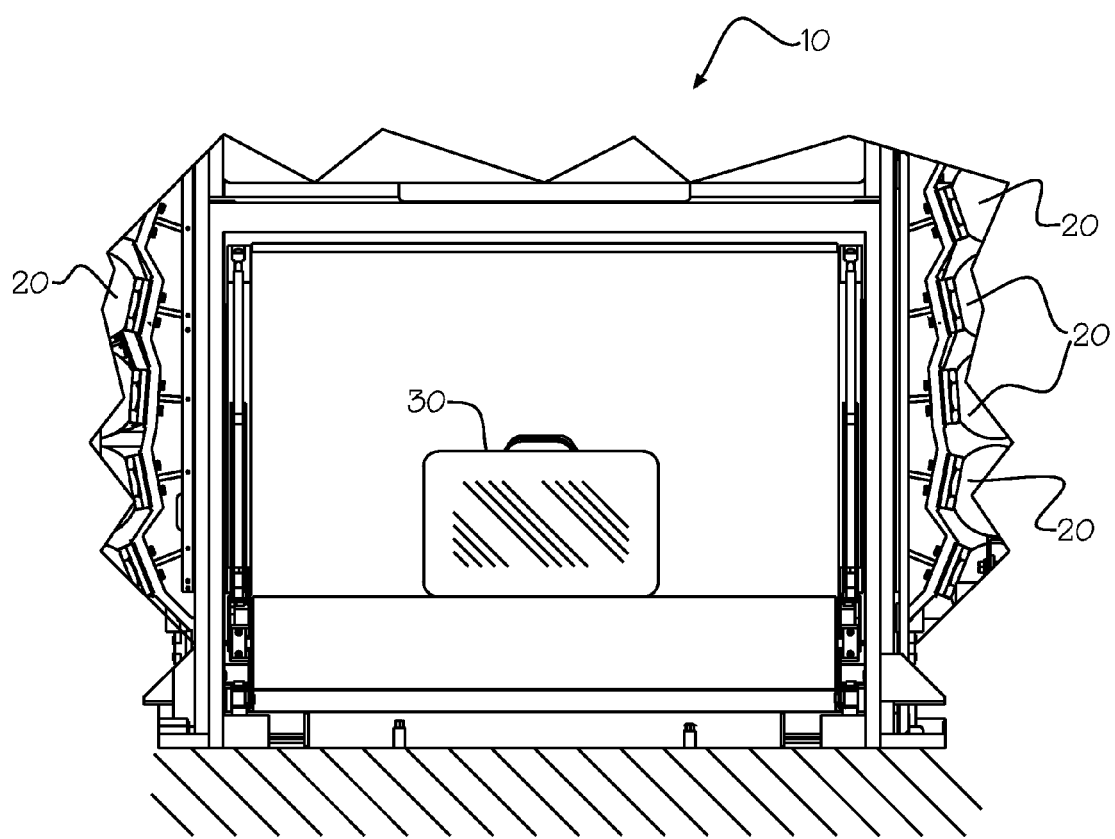
FIG. 1 is a partial end view of the apparatus used in XCT scanning and location of detector modules used to capture energy levels of electron beam after transit through package being inspected.
Figure 2:
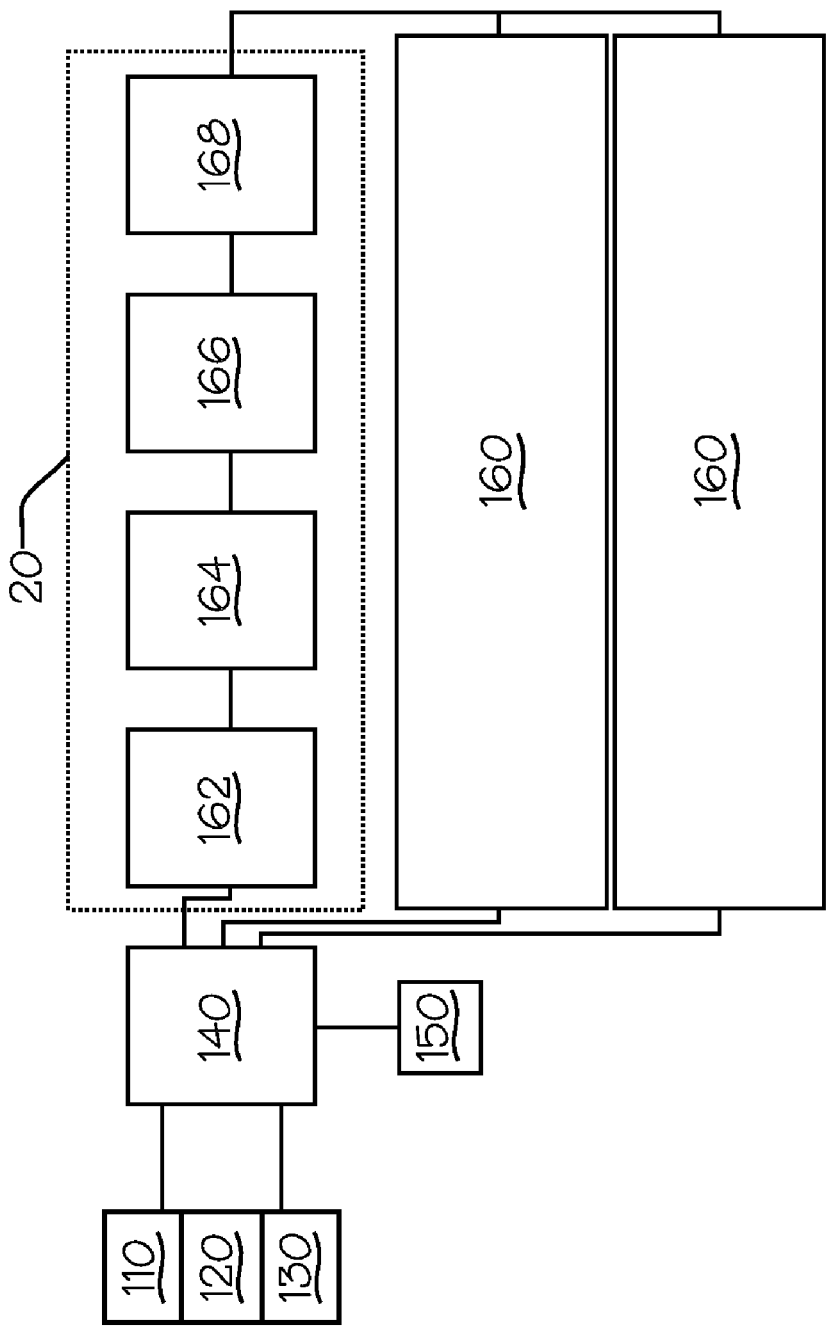
FIG. 2 is a block diagram of the processing and analysis assembly for the continuous high speed tomographic imaging system.
Figure 3:
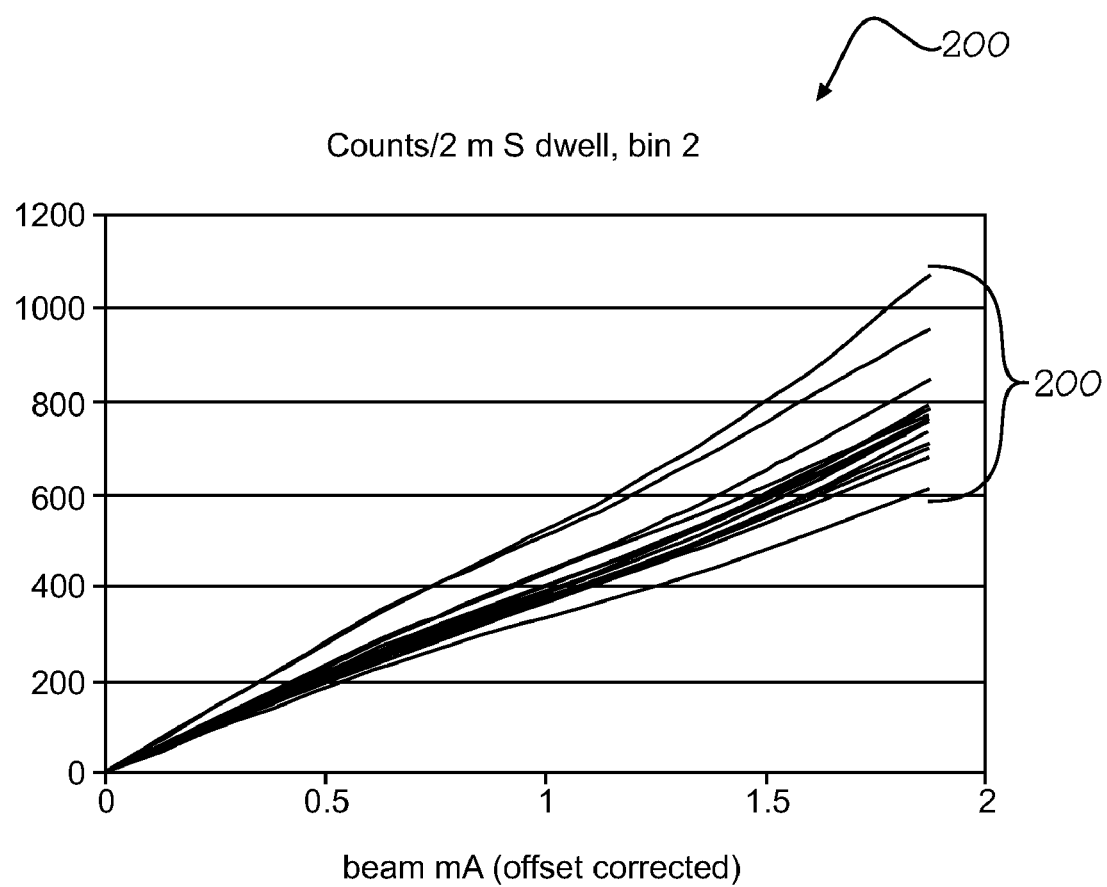
FIG. 3 is a plot of counts, which are the detector responses to the flux in a particular energy range, versus corrected mA beam current, which is proportional to the true X-ray flux, for several typical pixels.

The order of polynomial required to achieve correction to any particular accuracy depends on the amount of nonlinearity in the detectors and also on the range of operation. A quadratic or other simpler matching procedure is adequate to correct the nonlinearities illustrated in FIG. 3 to a precision of 1% up to about 400 counts. The accuracy of a quadratic fit degrades rapidly for higher flux as some of the pixels show counting rates both above and below the mean at different flux levels. At least a cubic polynomial is required for a good fit. For operation up to about 600 counts, the root mean squared error of a cubic polynomial fit to these pixels is one fourth of the error of the quadratic fit.

These detectors in the preferred embodiment are photon counting detectors, for which there are practically no noise counts or "dark current" when there is no X-ray flux. Thus the appropriate polynomials are homogeneous. That is, the 0 order coefficient $x_0$ is zero, the same for all pixels.

The counts in each pixel are matched with the best least squares fit to a third order homogeneous polynomial. That is, the best coefficients A, Q and Z are found to match the calibration counts from each pixel with the equation $$C(i) = A f(i) + Q f(i)^2 + Z f(i)^3.$$

The solution for these coefficients is $$\begin{pmatrix} A \\ Q \\ Z \end{pmatrix} = M^{-1} \begin{pmatrix} \overline{Cf} \\ \overline{Cf^2} \\ \overline{Cf^3} \end{pmatrix}$$

where $\overline{Cf}$ indicates the average of the product of the counts and the corrected currents over all the target current settings, etc., and $$M = \begin{bmatrix} \overline{f^2} & \overline{f^3} & \overline{f^4} \\ \overline{f^3} & \overline{f^4} & \overline{f^5} \\ \overline{f^4} & \overline{f^5} & \overline{f^6} \end{bmatrix}.$$

The mean squared error of this fit is $$S = \overline{C^2} + A^2 \overline{f^2} + Q^2 \overline{f^4} + Z^2 \overline{f^6} - 2(A\overline{Cf} + Q\overline{Cf^2} + Z\overline{Cf^3} - AQ\overline{f^3} - AZ\overline{f^4} - QZ\overline{f^5}).$$

The number of photons arriving at the pixel, which is the value to be computed as the corrected value for C, is $R = Af$. In terms of R, the best-fit polynomial is $$C = R + \frac{Q}{A^2} R^2 + \frac{Z}{A^3} R^3 \equiv R + \tau R^2 + \varsigma R^3 \quad (1)$$

where $$\tau \equiv \frac{Q}{A^2}.$$

$\tau$ is a scale factor with units of time per count or time per pulse which can be thought of as the pulse width.

Equation 1 can be written in the form $$C\tau = R\tau + (R\tau)^2 + \frac{\varsigma}{\tau^2}(R\tau)^3.$$

That is, any Cτ product with the same value of $$\xi = \frac{S}{\tau^2} = \frac{ZA}{Q^2}$$

has the same correction factor, $$\frac{R}{C} = \frac{R\tau}{C\tau}.$$

ξ is a dimensionless parameter that specifies the shape of the calibration curve. A two dimensional table, indexing values of Cτ and ξ, can contain all of the correction factors for unambiguous (i.e., correctable) counts. A 201×401 table, T(i, j), can contain the factors for correction within 1% rms error if an appropriate logarithmic scale is used for the values of ξ covering the range −20 to +20. The size of the bins and the range of Cσ are chosen to cover the range in the particular application.

The cubic polynomial is solved to determine the correction factor for each bin in the table, T. Assume that T is stored row by row. That is, the j index varies faster. For i=0 to 99:

$$\xi = -10^{\frac{(50-i)\log(400)}{100}}, a = \xi - \frac{1}{3}, b = \frac{2}{27} - \frac{\xi}{3} - \xi^2\tau, \gamma = \frac{b^2}{4} + \frac{a^3}{27}$$

For $j = 0$ to $400$  $T = .005j - 1.5$

If $y > 0, \alpha = \sqrt[3]{-\frac{b}{2} + \sqrt{\gamma}}$, $$\beta = \sqrt[3]{-\frac{b}{2} - \sqrt{\gamma}}, W = \alpha + \beta - \frac{1}{3}$$

else $\phi = \arccos\left(\frac{-b}{2\sqrt{-\frac{a^3}{27}}}\right), W = 2\sqrt{-\frac{a}{3}}\cos\left(\frac{\phi + 2\pi}{3}\right) - \frac{1}{3}$ $$T(i, j) = \frac{W}{\tau\xi}.$$

If $j = 300, (T = 0), T(i, j) = 1$

For i=100, ξ=0 and equation 1, above, reduces to a quadratic. The solution is thus the usual quadratic solution:

For j=0 to 400 τ=0.005j−1.5

If τ<−0.25 enter −99. Otherwise, $$T(i, j) = \frac{\sqrt{1+4\tau} - 1}{2\tau}.$$

For i=101 to 200, $$\xi = 10^{\frac{(i-50)\log(400)}{100}},$$

a and b, etc. are the same as above.

For $j = 0$ to $400$  $T = .005j - 1.5$

If $y > 0, W = \alpha + \beta - \frac{1}{3}$ else $W = 2\sqrt{-\frac{a}{3}}\cos\left(\frac{\phi}{3}\right) - \frac{1}{3}$ $$T(i, j) = \frac{W}{\tau\xi}.$$

If $j = 300, (T = 0), T(i, j) = 1$

There is always a solution to the cubic equation, even if the detector is far beyond saturation so that the correct solution is ambiguous. T is close to 1 for small τ, j≅300. Any pixel operating with τ with a larger magnitude than a value that would produce an unacceptably large correction can not be properly linearized. Therefore, starting at j=300, check if T is too far from 1.0. If so, enter a flag denoting operation beyond saturation in the table for all values of j that correspond to values of τ with larger magnitude.

At calibration, for each good pixel, store $$\tau = \frac{Q}{A^2}$$

and the row offset X(ξ):
For $$\xi > 0.05, i = \text{int}\left(150.5 + 100\frac{\log\xi}{\log 400}\right).$$

If i>200, set i=200. X=401i.
For $$\xi < -0.05, i = \text{int}\left(50.5 - 100\frac{\log(-\xi)}{\log 400}\right).$$

If i<0 set i=0. X=401i.
Otherwise, X=40100.
During operation, T is considered a one dimensional array. If a count of N is collected in a duration D, then let $$n = \text{int}\left\{\frac{200N\tau}{D} + 300.5\right\}.$$

The corrected count is R=N×T(n+X).

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An imaging apparatus for inspecting objects located within moving articles, said imaging inspection apparatus comprising:

a plurality of at least one imaging inspection device positioned on said frame and adapted for directing beams onto said articles as said articles through said inspection location substantially within said imaging apparatus to thereby inspect said articles, and for providing output signals as a result of said inspecting; and a processing and analysis assembly for receiving said output signals from said plurality of imaging inspection devices and for performing table lookups and simple multiplication, said table having a particular form adequate to correct nonlinearities matching a cubic polynomial; and including:

a) an offset X for said lookup, stored for each pixel having the nonlinearity shape parameter $\xi$ where if $$\xi > 0.05, \ i = \text{int}\left(150.5 + 100\frac{\log\xi}{\log 400}\right);$$

if $i \geq 200$, set $i=200$, Then $X=401i$; if $$\xi < -0.05, \ i = \text{int}\left(50.5 - 100\frac{\log(-\xi)}{\log 400}\right);$$

if $i \leq 0$, set $i=0$, Then $X=401i$; otherwise, $X=40100$;

b) the parameter $\tau$ also stored for each pixel; and
c) a count of N is collected in a dwell of duration D, then the correction factor is stored at location X+n in said table where $$n = \text{int}\left\{\frac{200N\tau}{D} + 300.5\right\}$$

where:
X is an integer value,
i is an integer,
$\tau$ is a scale factor with units of time per count or time per pulse, and
n is an integer.

2. The imaging apparatus of claim 1, wherein said plurality of imaging inspection devices each comprises an X-ray computer tomography (XCT) scanning device and said beams are X-rays.

3. The imaging apparatus of claim 2, wherein said XCT scanning devices are positioned on said frame in at least three groupings, each grouping of said XCT scanning devices being positioned relative to said inspection location and adapted for directing said X-rays along a different plane onto only said main portion within said inspection location substantially within said imaging apparatus, each of said planes being substantially perpendicular to said inspection location.

4. The imaging apparatus of claim 3, further including at least one X-ray detector positioned on said frame relative to said main portion of said inspection location and adapted for receiving said X-rays from selected ones of said XCT scanning devices as said X-rays pass through said articles at said inspection location.

5. In an imaging apparatus for inspecting objects located within moving articles, said imaging inspection apparatus having at least one imaging inspection device positioned on said frame and adapted for directing beams onto said articles as said articles pass through said inspection location substantially within said imaging apparatus to thereby inspect said articles, and for providing output signals as a result of said inspecting, the improvement comprising:

a processing and analysis assembly adapted for receiving said output signals from said plurality of imaging inspection devices and for accessing correction factors, said processing and analysis assembly performing steps comprising:

a) storing $$\tau = \frac{Q}{A^2}$$

and the row offset $X(\xi)$:
b) storing the table T; and
c) accessing the correction factor $T(n+X)$; if a count of N is collected in a dwell of duration D, $$n = \text{int}\left\{\frac{200N\tau}{D} + 300.5\right\}$$

where:
$\tau$ is a scale factor with units of time per count or time per pulse,
Q is a unit of time,
A is a dimension of a pixel receiving photons,
$\xi$ is a dimensionless parameter,
n is an integer,
N$\tau$ is a product of a number of photon counts and a scale factor, and
X is an integer value.

6. The imaging apparatus of claim 5, wherein said imaging inspection devices each comprises an X-ray computer tomography (XCT) scanning device and said beams are X-rays.

7. The imaging apparatus of claim 6, wherein said XCT scanning devices are positioned on said frame in at least three groupings, each grouping of said XCT scanning devices being positioned relative to said inspection location and adapted for directing said X-rays along a different plane onto only said main portion within said inspection location located substantially within said imaging apparatus, each of said planes being substantially perpendicular to said inspection location.

8. The imaging apparatus of claim 7, further including at least one X-ray detector positioned on said frame relative to said main portion of said inspection location for receiving said X-rays from selected ones of said XCT scanning devices as said X-rays pass through said articles at said inspection location.

9. In an imaging apparatus for inspecting objects located within moving articles, said imaging inspection apparatus having at least one imaging inspection device positioned on said frame and adapted for directing beams onto said articles as said articles pass through said inspection location substantially within said imaging apparatus to thereby inspect said articles, and for providing output signals as a result of said inspecting, the improvement comprising a process of inspecting objects, the steps comprising providing a processing and analysis assembly adapted for receiving said output signals from said plurality of imaging inspection devices and for retrieving correction factors derived by matching the nonlinearities of the imaging apparatus pixels to cubic equations, the steps comprising correcting N counts, collected in time D, to NT(X+n), the substeps comprising:
  i) accessing τ and the row offset X(ξ);
  ii) computing the index $$n = \text{int}\left\{\frac{200N\tau}{D} + 300.5\right\};$$

and
  iii) accessing T(X+n) where:
    τ is a scale factor with units of time per count or time per pulse,
    ξ is a dimensionless parameter,
    Nτ is a product of a number of photon counts and a scale factor,
    n is an integer,
    X is an integer value, and
    T is a two-dimensional table containing correction factors.

10. The imaging apparatus of claim 9, wherein said imaging inspection devices each comprises an X-ray computer tomography (XCT) scanning device and said beams are X-rays.

11. The imaging apparatus of claim 10, wherein said XCT scanning devices are positioned on said frame in at least three groupings, each grouping of said XCT scanning devices being positioned relative to said inspection location and adapted for directing said X-rays along a different plane onto only said main portion within said inspection location located substantially within said imaging apparatus, each of said planes being substantially perpendicular to said inspection location.

12. The imaging apparatus of claim 11, further including at least one X-ray detector positioned on said frame relative to said main portion of said inspection location and adapted for receiving said X-rays from selected ones of said XCT scanning devices as said X-rays pass through said articles at said inspection location.

* * * * *